(12) United States Patent
Wright et al.

(10) Patent No.: US 10,709,482 B2
(45) Date of Patent: Jul. 14, 2020

(54) LAMINOPLASTY SYSTEM

(75) Inventors: Nick Wright, Philadelphia, PA (US); Thomas Shinn, Collegeville, PA (US); Michael Evangelist, Pottstown, PA (US); Jon Suh, Blue Bell, PA (US)

(73) Assignee: Globus Medical, Inc., Audubon, PA (US)

( * ) Notice: Subject to any disclaimer, the term of this patent is extended or adjusted under 35 U.S.C. 154(b) by 126 days.

(21) Appl. No.: 13/484,069

(22) Filed: May 30, 2012

(65) Prior Publication Data

US 2013/0325022 A1 Dec. 5, 2013

(51) Int. Cl.
| A61B 17/70 | (2006.01) |
| A61B 17/02 | (2006.01) |
| A61B 17/88 | (2006.01) |
| A61B 17/00 | (2006.01) |

(52) U.S. Cl.
CPC ........ *A61B 17/7071* (2013.01); *A61B 17/025* (2013.01); *A61B 17/7074* (2013.01); *A61B 17/8866* (2013.01); *A61B 2017/00473* (2013.01); *A61B 2017/0256* (2013.01)

(58) Field of Classification Search
CPC ... A61B 17/02; A61B 17/0206; A61B 17/025; A61B 17/66; A61B 17/663; A61B 17/7068; A61B 17/7062–707; A61B 17/7071; A61B 2017/0256; A61B 2017/681; A61F 2/4455; B25B 3/00; B25B 5/04; B25B 7/00; B25B 7/20
USPC ....... 600/210, 213, 215, 217, 222, 226, 235; 606/86 R, 90, 105; 254/95, 96, 12, 230, 254/2 B, 100, 103
See application file for complete search history.

(56) References Cited

U.S. PATENT DOCUMENTS

| 18,760 | A | * | 12/1857 | Miller | 254/103 |
| 235,481 | A | * | 12/1880 | Williams | 74/577 R |
| 382,245 | A | * | 5/1888 | Stadler | 254/95 |
| 538,392 | A | * | 4/1895 | Sheridan et al. | 254/103 |
| 592,226 | A | * | 10/1897 | Ingram et al. | 254/230 |
| 605,848 | A | * | 6/1898 | Borst | 254/230 |
| 704,403 | A | * | 7/1902 | Thill | 248/200.1 |
| 761,413 | A | * | 5/1904 | Schroer | 254/100 |
| 789,071 | A | * | 5/1905 | Schroer | 254/98 |
| 858,716 | A | * | 7/1907 | Gilchrist | 254/95 |
| 1,029,447 | A | * | 6/1912 | Jantzen | 74/396 |
| 1,261,003 | A | * | 4/1918 | Baboock et al. | 254/100 |
| 1,325,414 | A | * | 12/1919 | Hummer | 254/100 |
| 1,401,190 | A | * | 12/1921 | Risley | 600/215 |
| 1,440,627 | A | * | 1/1923 | Rasmussen et al. | 254/230 |

(Continued)

OTHER PUBLICATIONS

Hong et al., "Measurement of the Normal Lumbar Intervertebral Disc Space Using Magnetic Resonance Imaging", 2010, Asian Spine Journal, vol. 4, No. 1, pp. 1-6.*

(Continued)

*Primary Examiner* — Amy R Sipp (57) ABSTRACT

A distractor device is disclosed that distracts and holds open an intralaminar space. The distractor device has a housing that includes a kickstand, an actuating bar that includes a foot, and an actuator that engages and drives the actuating bar, wherein the kickstand is configured to engage a first portion of a lamina on one side of the intralaminar space and the foot is configured to engage a second portion of the lamina on another side of the intralaminar space.

16 Claims, 5 Drawing Sheets

(56) References Cited

U.S. PATENT DOCUMENTS

| | | | |
|---|---|---|---|
| 1,487,437 A * | 3/1924 | Brune, Sr. | 254/100 |
| 1,550,885 A * | 8/1925 | Dart | 254/100 |
| 1,554,277 A * | 9/1925 | Hackmann | 254/95 |
| 1,555,765 A * | 9/1925 | Smith | 254/100 |
| 1,848,765 A * | 3/1932 | Cantwell | 254/100 |
| 2,426,717 A * | 9/1947 | Uhlenkott | 254/100 |
| 2,933,288 A * | 4/1960 | Sholick | 254/12 |
| 3,984,732 A * | 10/1976 | Podrecca | 361/219 |
| 4,777,939 A * | 10/1988 | Kees et al. | 600/217 |
| 5,020,519 A * | 6/1991 | Hayes et al. | 606/237 |
| 5,458,641 A * | 10/1995 | Ramirez Jimenez | A61F 2/44 403/43 |
| 5,720,751 A * | 2/1998 | Jackson | 606/86 R |
| 5,891,017 A * | 4/1999 | Swindle et al. | 600/205 |
| 6,066,175 A | 5/2000 | Henderson | |
| 6,080,157 A | 6/2000 | Cathro | |
| 6,159,212 A * | 12/2000 | Schoedinger, III | A61B 17/8866 606/279 |
| 6,235,059 B1 | 5/2001 | Benezech | |
| 6,491,695 B1 * | 12/2002 | Roggenbuck | A61B 17/8866 606/105 |
| 6,533,791 B1 * | 3/2003 | Betz | A61B 17/025 606/247 |
| 6,572,619 B2 | 6/2003 | Santilli | |
| 6,635,087 B2 | 10/2003 | Angelucci | |
| 6,660,007 B2 | 12/2003 | Khanna | |
| 6,849,076 B2 * | 2/2005 | Blunn et al. | 606/105 |
| 6,908,469 B2 * | 6/2005 | Sellers et al. | 606/105 |
| 7,112,222 B2 | 9/2006 | Fraser | |
| 7,311,294 B1 * | 12/2007 | Ruan | 254/108 |
| 7,371,239 B2 * | 5/2008 | Dec et al. | 606/279 |
| 7,955,392 B2 * | 6/2011 | Dewey | A61B 17/7068 606/248 |
| 8,377,130 B2 * | 2/2013 | Moore | A61F 2/4611 606/86 R |
| 8,556,975 B2 * | 10/2013 | Ciupik et al. | 623/17.15 |
| 8,632,548 B2 * | 1/2014 | Soubeiran | 606/90 |
| 8,636,656 B2 * | 1/2014 | Nichter et al. | 600/228 |
| 8,641,723 B2 * | 2/2014 | Connor | 606/105 |
| 8,998,955 B2 * | 4/2015 | Calvosa et al. | 606/249 |
| 2002/0120335 A1 | 8/2002 | Angelucci | |
| 2003/0176926 A1 * | 9/2003 | Boehm, Jr. | A61F 2/446 623/17.16 |
| 2004/0030388 A1 | 2/2004 | Null | |
| 2004/0073214 A1 * | 4/2004 | Mehdizadeh | A61B 17/8866 606/86 A |
| 2005/0171541 A1 * | 8/2005 | Boehm, Jr. | A61B 17/3417 623/17.16 |
| 2005/0177235 A1 * | 8/2005 | Baynham | A61F 2/447 623/17.11 |
| 2005/0251138 A1 | 11/2005 | Boris | |
| 2005/0253123 A1 * | 11/2005 | Sonnenberg | 254/100 |
| 2006/0111726 A1 * | 5/2006 | Felt et al. | 606/86 |
| 2007/0123989 A1 * | 5/2007 | Gfeller | A61B 17/562 623/17.16 |
| 2007/0270968 A1 * | 11/2007 | Baynham | A61F 2/447 623/17.11 |
| 2007/0299315 A1 * | 12/2007 | Geller | 600/217 |
| 2008/0033440 A1 * | 2/2008 | Moskowitz | A61B 17/0642 606/251 |
| 2008/0249622 A1 * | 10/2008 | Gray | A61F 2/4455 606/86 A |
| 2008/0287997 A1 * | 11/2008 | Altarac et al. | 606/249 |
| 2008/0319481 A1 * | 12/2008 | Moore | A61B 17/14 606/246 |
| 2009/0138045 A1 * | 5/2009 | Ciupik et al. | 606/249 |
| 2010/0016968 A1 * | 1/2010 | Moore | A61B 17/14 623/17.11 |
| 2010/0241230 A1 * | 9/2010 | Mazzuca et al. | 623/17.11 |
| 2011/0077738 A1 * | 3/2011 | Ciupik | A61F 2/4455 623/17.11 |
| 2011/0101289 A1 * | 5/2011 | Lee | 254/103 |
| 2011/0106083 A1 | 5/2011 | Voellmicke | |
| 2011/0106087 A1 | 5/2011 | Gamache | |
| 2011/0106169 A1 | 5/2011 | Zalenski | |
| 2011/0172774 A1 * | 7/2011 | Varela | A61F 2/447 623/17.16 |
| 2012/0029565 A1 * | 2/2012 | Seifert et al. | 606/249 |
| 2012/0149990 A1 * | 6/2012 | Buehler et al. | 600/210 |
| 2012/0232658 A1 * | 9/2012 | Morgenstern Lopez et al. | 623/17.16 |
| 2012/0259344 A1 * | 10/2012 | Johnston, Jr. | 606/105 |
| 2013/0110113 A1 * | 5/2013 | Glazer | A61B 17/7077 606/90 |
| 2013/0274819 A1 * | 10/2013 | Horvath | 606/86 R |
| 2013/0317312 A1 * | 11/2013 | Eastlack et al. | 600/215 |
| 2013/0325022 A1 * | 12/2013 | Wright et al. | 606/90 |

OTHER PUBLICATIONS

Tonosu et al., "Consideration of proper operative route for interlaminar approach for percutaneous endoscopic lumbar discectomy", 2016, Journal of Spine Surgery, 2(4), pp. 281-288.*

* cited by examiner

LAMINOPLASTY SYSTEM

BACKGROUND OF THE PRESENT DISCLOSURE

1. Field of the Present Disclosure

The present disclosure is generally directed to a system to distract, as well as control and maintain a distraction of a space, such as, for example, during an open door laminoplasty surgery.

2. Related Art

Generally, laminoplasty is a spine surgery that may involve reshaping or repositioning bone to relieve excess pressure on the spinal nerves in the cervical spine or neck. Pressure on the spinal cord might be due to various reasons such as degenerative changes, disc herniations, tumors, fractures, arthritis, bone spurs, or the like.

Presently, there are no instruments available to infinitely control the level of distraction during a laminoplasty surgery, such as, e.g., an open door laminoplasty procedure. For example, laminoplasty surgery may include manual techniques by a surgeon to open the intralaminar space, including pushing on the spinous process to partially crack the contralateral lamia to open the instralaminar space, which is inherent to overdistraction and complete fracture of contralateral lamina.

There is a need for a system to distract a space, as well as to control and maintain a distraction of, e.g., an intralaminar space during procedures such as, e.g., open door laminoplasty procedure.

SUMMARY OF THE PRESENT DISCLOSURE

The present disclosure meets the foregoing by providing a system and a device for distracting a space, such as, e.g., an intralaminar space, and holding the space open for an extended period of time, as may be required.

According to an aspect of the disclosure, a distractor device is disclosed that distracts and holds open an intralaminar space. The distractor device comprises: a housing that includes a kickstand; an actuating bar that includes a foot; and an actuator that engages and drives the actuating bar, wherein the kickstand is configured to engage a first portion of a lamina on one side of the intralaminar space and the foot is configured to engage a second portion of the lamina on another side of the intralaminar space. The actuating bar may be at least partially inserted in the housing. The distractor device may further comprise a stop that disallows the actuating bar from coming out of the housing and that prevents over distraction. The stop may comprise a pin. At least one of the actuator and the actuating bar may comprise a threading. The actuator may comprise a worm gear. The housing may comprise a recess that is configured to engage a protrusion on a destractor holder. The housing may comprise a plurality of recesses that are configured to engage a plurality of respective protrusions on a distractor holder to provide multiple points of fixation. The multiple points of fixation may comprise six points of fixation.

According to another aspect of the disclosure, a distractor holder is provided for distracting and holding open an intralaminar space. The distractor holder comprises: a pair of scissor members; and an offset, wherein the offset includes a distractor holder tip. The distractor holder may further comprise a cannula that is aligned with a portion of the offset to guide a driver portion of a driver. The offset may comprise a distractor holder tip. The distractor holder tip may comprise a protrusion that is engageable with a portion of a distractor device. The distractor holder tip may comprise a plurality of protrusion that are engageable with portions of a distractor device to provide multiple points of fixation. The multiple points of fixation may comprise six points of fixation.

Additional features, advantages, and aspects of the present disclosure may be set forth or apparent from consideration of the following detailed description, drawings, and claims. Moreover, it is to be understood that both the foregoing summary of the present disclosure and the following detailed description are exemplary and intended to provide further explanation without limiting the scope of the present disclosure as claimed.

BRIEF DESCRIPTION OF THE DRAWINGS

The accompanying drawings, which are included to provide a further understanding of the present disclosure, are incorporated in and constitute a part of this specification, illustrate aspects of the present disclosure and together with the detailed description serve to explain the principles of the present disclosure. No attempt is made to show structural details of the present disclosure in more detail than may be necessary for a fundamental understanding of the present disclosure and the various ways in which it may be practiced. In the drawings.

DETAILED DESCRIPTION OF THE PRESENT DISCLOSURE

The aspects of the present disclosure and the various features and advantageous details thereof are explained more fully with reference to the non-limiting aspects and examples that are described and/or illustrated in the accompanying drawings and detailed in the following description. It should be noted that the features illustrated in the drawings are not necessarily drawn to scale, and features of one aspect may be employed with other aspects as the skilled artisan would recognize, even if not explicitly stated herein. Descriptions of well-known components and processing techniques may be omitted so as to not unnecessarily obscure the aspects of the present disclosure. The examples used herein are intended merely to facilitate an understanding of ways in which the present disclosure may be practiced and to further enable those of skill in the art to practice the aspects of the present disclosure. Accordingly, the examples and aspects herein should not be construed as limiting the scope of the present disclosure, which is defined solely by the appended claims and applicable law. Moreover, it is noted that like reference numerals represent similar parts throughout the several views of the drawings.

The word "surgeon," as used in this disclosure, means any person that uses the disclosure to distract a space for surgery. Such a person may be educated, certified, and trained to perform surgical procedures. Such a person may also be a lay person with no experience in the surgical field. In addition, such a person may have a skill-set, education, and/or knowledge base which falls somewhere between a person who may be educated, certified, and trained to perform surgical procedures and a lay person.

Surgical intervention for back/neck conditions is usually reserved for people with chronic back pain or related impairment, perhaps for which other treatments have failed. A surgical procedure may be required for people who have conditions that may have caused narrowing of the spinal canal, for example. The narrowing may have happened as a result of degeneration of the facet joints and/or the invertebral discs. Laminoplasty surgery may generally relieve pressure on the spinal nerves by removing or reducing a source of pressure. The procedure may comprise open door laminoplasty, which may involve "hinging" one side of the posterior elements of the vertebrae and cutting the other side so that it forms a "door" which is opened and held in place with wedges or the like, often made of bone and instrumentation. The present disclosure provides for a system for controlling and maintaining the distraction of the intralaminar space during such a procedure. For example, after a surgeon cuts through the lamina of the cervical or upper thoracic spine and makes a partial cut on the contralateral side, a distraction device described herein may be placed in the cut using a distraction holder, also described herein, which together may be used to infinitely distract and hold that space open for an extended period of time.

Figures 1A, 1C:
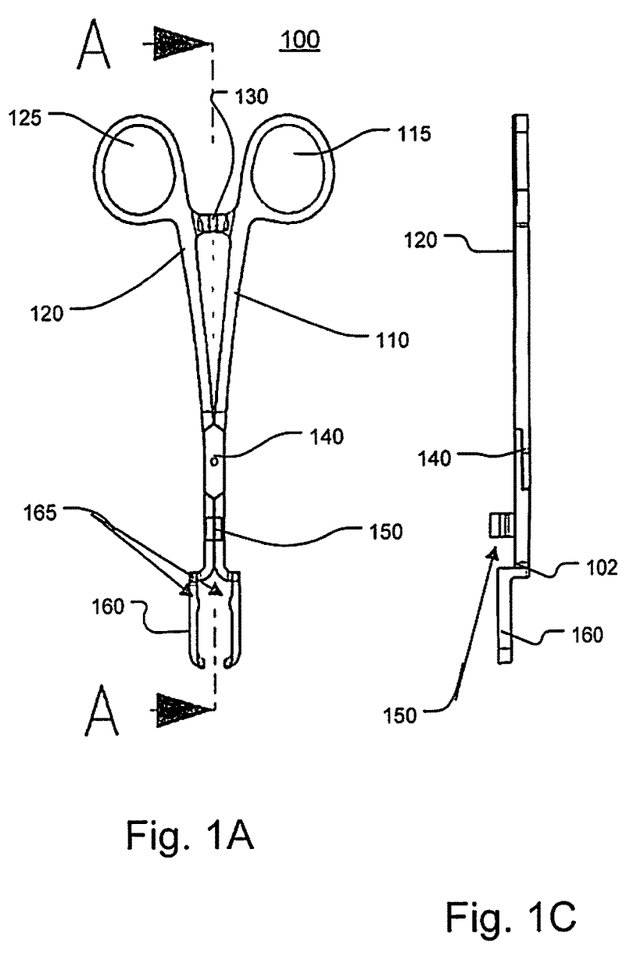
FIG. 1A shows a front view of an example of a distractor holder, constructed according to the principles of the present disclosure.
FIG. 1C shows a side of the distractor holder of FIG. 1A.

FIG. 1A shows a front view of an example of a distractor holder 100, constructed according to the principles of the present disclosure. The distractor holder 100 may include a scissor holder configured with a pair of scissor members 110, 120, rotatably attached at a fulcrum point 140 to permit the two scissor members 110, 120 to open and close a detractor holder tip 160 that may be configured at one end of the distractor holder 100. The two scissor members 110, 120 may be configured with openings 115, 125, respectively, for a thumb/finger combination of a user to control motion of the distractor holder 100 for opening and closing the detractor holder tip 160.

The distractor holder 100 may include a locking member 130 that may operate as a lock and key to securely hold a distractor device 200 (shown in FIG. 3A) in the distractor holder tip 160. The distractor holder tip 160 may include at least one holding protrusion 165. For instance, the distractor holder tip 160 may include a pair of holding protrusions 165 (shown in FIG. 1A), or it may include three or more holding protrusions. The locking member 130 may include a pair of engaging protrusions formed integrally with (or attached to) the scissor members 110, 120, and configured to engage and lock to each other, as is known in the art. The pair of engaging protrusions may include discrete interlocking stages, as is known in the art, so that the scissor members 110, 120 may include a plurality of discrete locking positions with respect to each other.

Figure 2A:
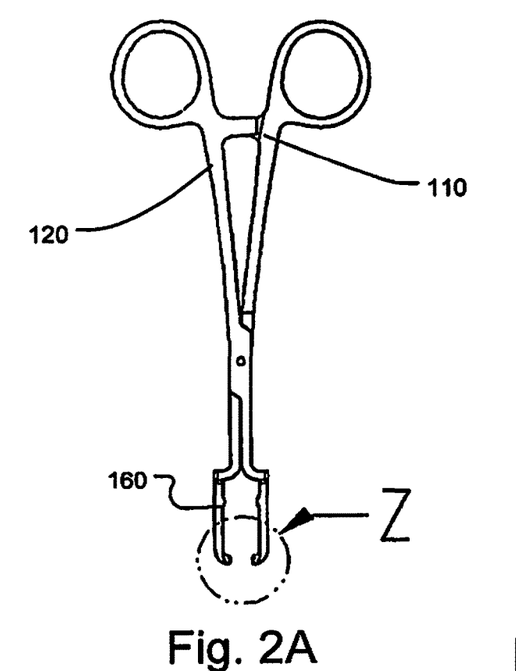
FIG. 2A shows a front view of the distractor holder of FIG. 1A, having a region Z that is shown in enlarged view in FIGS. 2B and 2C.
Figure 3A:
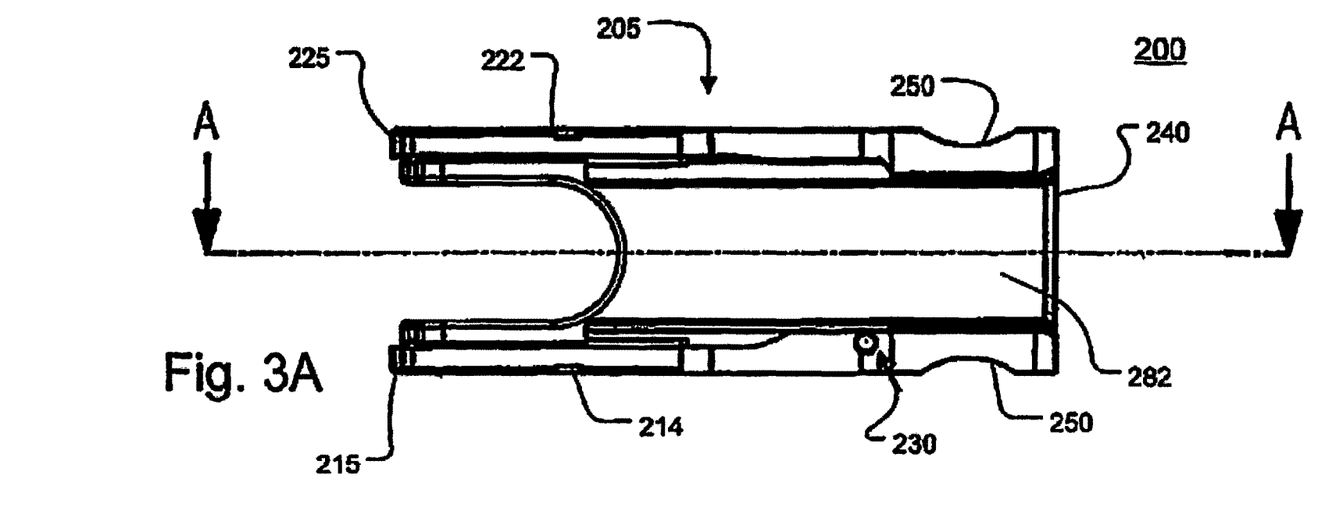
FIG. 3A shows a back view of an example of a distractor device, constructed according to the principles of the disclosure.
Figure 3B:
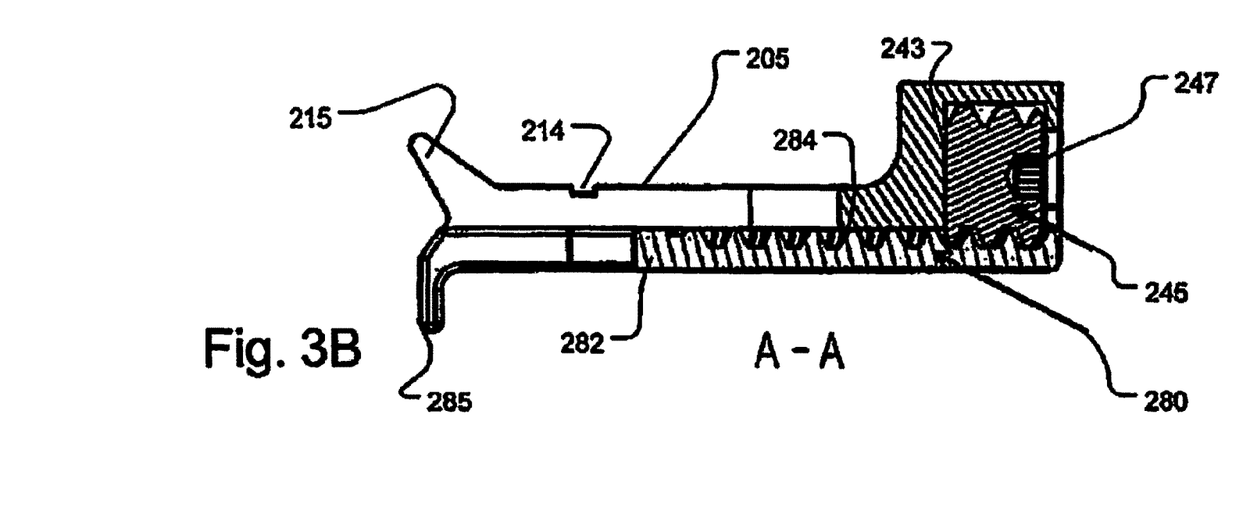
FIG. 3B shows a cross-section view of the distractor device cut along the line A-A in FIG. 3A.

The distractor holder 100 may further include a cannula 150, which may be configured to receive and allow pass-through and align/guide of, e.g., a portion 310 of a driver 300 (shown in FIGS. 5A, 5B) so as to engage an actuator 245 (shown in FIG. 3B). The cannula 150 may be integrally formed with (or attached to) either, or both of the scissor members 110, 120. For example, the cannula 150 may be formed as an opening in a protrusion on the scissor member 110 (120), or an opening that is formed by a pair of protrusions located (or integrally formed with) on the scissor members 110, 120, when the distractor holder 100 is substantially closed (e.g., shown in FIG. 2A).

Figure 1B:
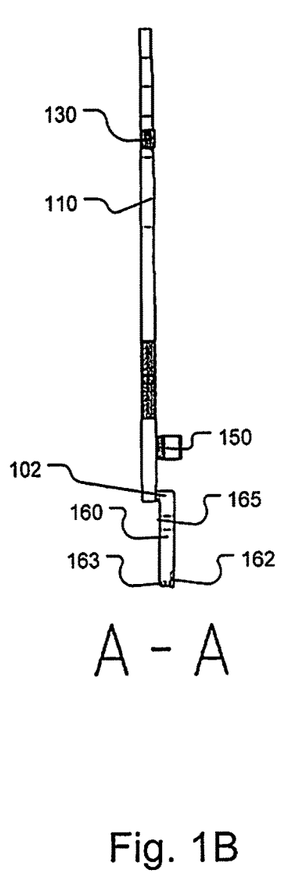
FIG. 1B shows a cross-section cut view of the distractor holder of FIG. 1A, cut along the line A-A.

FIG. 1B shows a cross-section cut view of the distractor holder 100 of FIG. 1A, cut along the line A-A and viewed in the direction of the arrows.

FIG. 1C shows a side of the distractor holder 100.

As seen in FIGS. 1B and 1C, the distractor holder 100 may include an offset 102 just below the cannula 150, which may aid in alignment of the cannula 150, the distractor holder 100, the actuator 245, and the driver 300, while also allowing the user easier control of the multiple parts of the system during use.

Figure 2B:
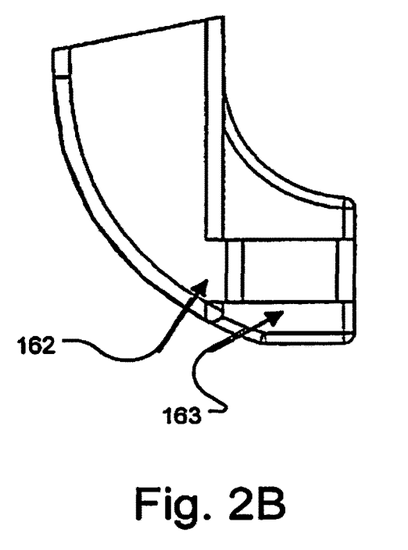
FIGS. 2B and 2C are enlarged views of the region Z shown in FIG. 2A.
Figure 2C:
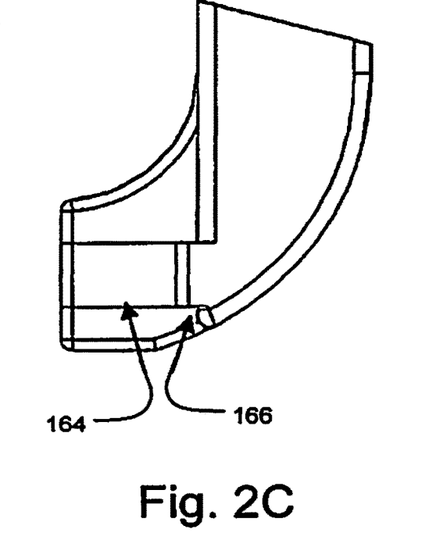

FIG. 2A shows a front view of the distractor holder 100, having a region Z of the detractor holder tip 160, which is shown in enlarged view in FIGS. 2B and 2C. FIG. 2B shows an enlarged view of the region Z of the scissor member 110. FIG. 2C shows an enlarged view of the region Z of the scissor member 120.

Referring to FIGS. 2B and 2C, the scissor member 110 may include one or more protrusions 165 and a plurality of keyed protrusions 162, 163; and, the scissor member 120 may include one or more protrusions 165 and a plurality of keyed protrusions 164, 166. The protrusions 165 may be configured to engage and mate with a pair of recesses 250 in the distractor device 200 (shown in FIG. 3A). The protrusions 165 may be configured on a proximal portion of the distractor holder tip 160. The keyed protrusions 162, 164 may be configured to engage and mate with, for example, keyed recesses 214, 222, provided on the distractor device 200. The keyed protrusions 163, 166 may be configured to engage and mate with another set of keyed recesses (not shown) provided on the distractor device 200. Together, the protrusions 162, 164, 165, and 163, 166, 165, may constitute six keyed points of fixation (e.g., three points of fixation per scissor member 110, 120). The protrusions 162-166 may have any shape, including, for example, a rounded shape, a square shape, a triangular shape, a semi-spherical shape, a cube shape, a pyramid shape, or any other shape, or any combination of the foregoing.

FIG. 3A shows a back view of an example of a distractor device 200, constructed according to the principles of the disclosure. FIG. 3B shows a cross-section view of the distractor device 200 cut along the line A-A and viewed in the direction of the arrows in FIG. 3A.

Referring to FIGS. 3A and 3B, the distractor device 200 includes a housing 205 and an actuator assembly 245, 280. The actuator assembly may include, e.g., a worm gear actuator 245 and an actuating bar 280 that can control a height (or length) of the actuating bar 280 with respect to the housing 205. The actuator 245 may include, e.g., a threaded bolt that has a substantially flat surface 243 on one side (shown in FIG. 3B) and a substantially flat surface and an engageable opening 247 (e.g., a hex-screw opening, a Phillips head opening, a common-head opening, or the like) on the other, opposite side 240. The actuator 245 may be configured to be inserted into the housing 205 and to prevent expulsion from the housing 205 after it has been properly seated in the housing 205. The actuating bar 280 may include a longitudinal member 282 and a plurality of threads 284 that are configured to engage and be driven by, e.g., the threads on the actuator 245. The longitudinal member 282 may include a flat portion that may be visible in the distraction device 200 from, e.g., the back side. The actuating bar 280 may further include a pair of feet 285 at an end opposite the end comprising the threads 284. The actuating bar 280 may include a semi-circular cut-out, as seen in FIG. 3B. Still further, the actuating bar 280 may include edge portions (not shown) that may engage respective guides (not shown) in the housing 205 to properly align and guide the actuating bar 280 as it moves along a longitudinal axis of the housing 205 (e.g., an axis that is substantially parallel with the line A-A in FIG. 3A).

The housing 205 may include an opening (not shown) that is configured to receive the actuating bar 280 and to allow the actuating bar 280 to be slidably placed inside the housing 205. The housing 205 may further include one or more channels (not shown) that are configured to receive, slidably guide and hold the actuating bar 280 in the housing 205. The channel may be configured to slidably engage portions of the actuating bar 280, such as, for example, edge portions (not shown) and provide a substantially tight fit of the actuating bar 280 in the housing 205, to minimize any or eliminate substantially entirely free play between the actuating bar 280 and the housing 205. The housing may include a cut-out find window portion (as seen, e.g., in FIG. 3A) through which the surgery area and/or the actuating bar 280 may be visible. The housing 205 may further include a stop holder (not shown) that is configured to receive and hold a stop 230 that disallows the actuating bar 280 from coming out of the housing 205, and to provide a stop to prevent over distraction. The stop 230 may include, e.g., a pin, a screw, a rod, a rivet, a bolt, or the like.

The housing 205 may include the plurality of recesses 214, 222, 250. The housing 205 includes a pair of kickstands 215, 225. The plurality of recesses 214, 222, 250, may be configured to engage and mate with the protrusions 164, 162 provided in the detractor holder tip 160, thereby allowing the detractor housing 205 to be properly aligned and securely nested in the detractor holder 100. The plurality of recesses 214, 222, 250 may include, for example, cavities or indentations that may be configured to receive protrusions 162-166.

The distractor device 200 may be assembled by, for example, inserting and properly seating the actuator 245 in the housing 205. Once the actuator 245 has been inserted into and properly seated in the housing 205, the actuating bar 280 may be placed into the housing by, e.g., properly aligning the actuating bar 280 with the opening in the housing 205 and/or the channels in the housing 205 and inserting the actuating bar 280 into the housing 205 through the opening. The actuating bar 280 may be pushed into the housing 205 until it contacts a portion (e.g., a thread) of the actuator 245. Once the actuator 245 and actuating bar 280 contact, the actuator 245 may be manipulated (e.g., turned) to engage and slidably move the actuating bar 280 further into the housing 205. Once the actuating bar 280 is seated in the housing 205, the stop 230 may be inserted into the housing 205 to disallow the actuating bar 280 from coming out from the housing 205. As mentioned earlier, the stop 230 may also provide a stop for the actuating bar 280 to prevent over distraction.

Figure 4A:
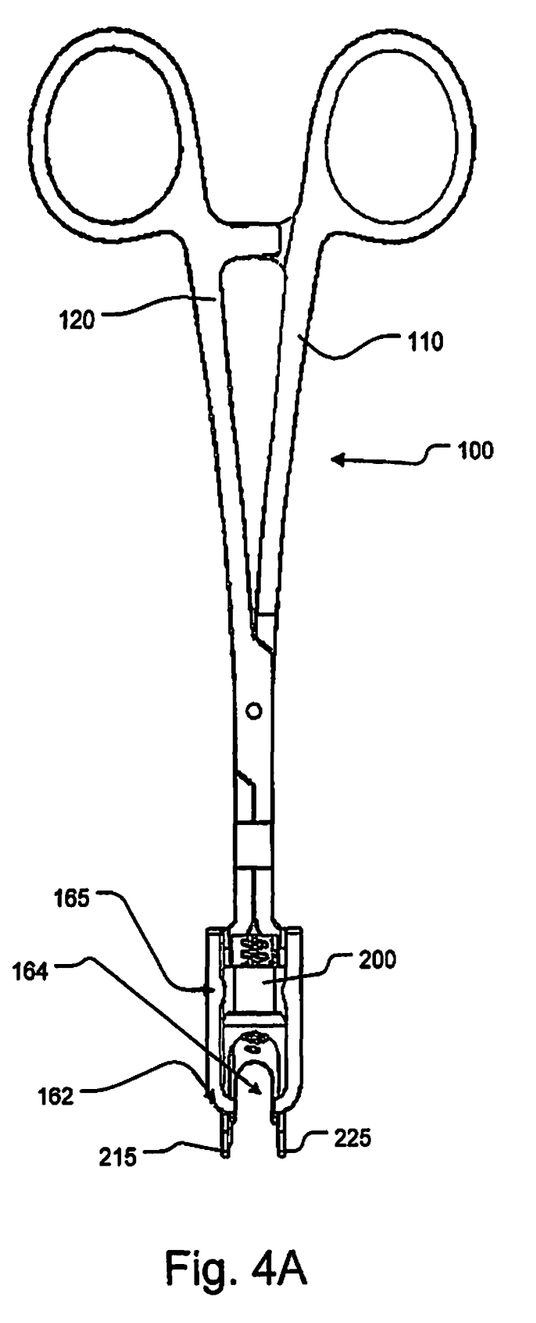
FIG. 4A shows a front view of an example of a distractor holder and a distractor device, constructed according to the principles of the disclosure.
Figure 4B:
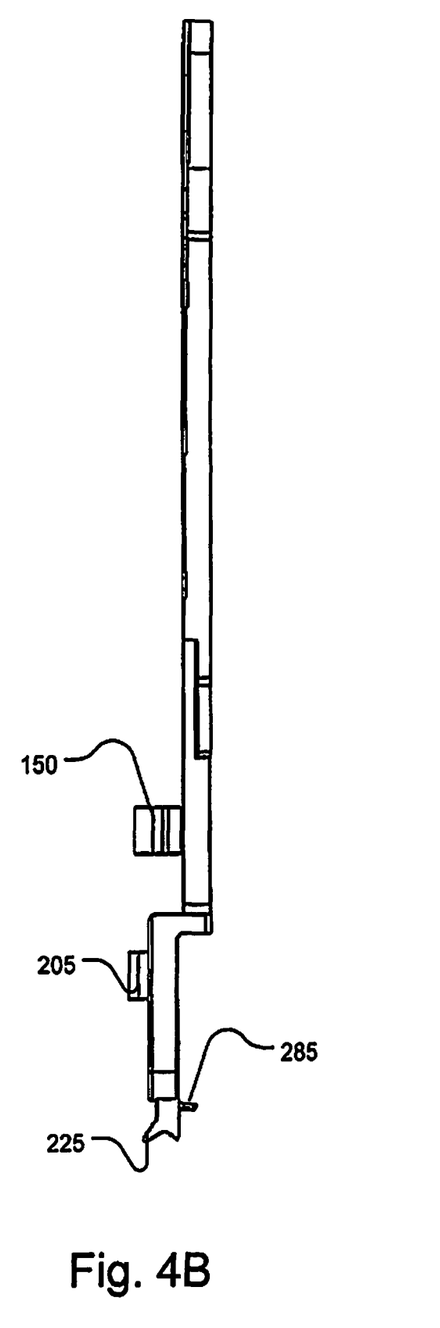
FIG. 4B shows a side of the distractor holder of FIG. 4A.

FIG. 4A shows a front view of the distractor holder 100 and the distractor device 200. FIG. 4B shows a side of the distractor holder 100 with the distractor device 200 securely nested in the distractor holder tip 160.

Figure 5A:
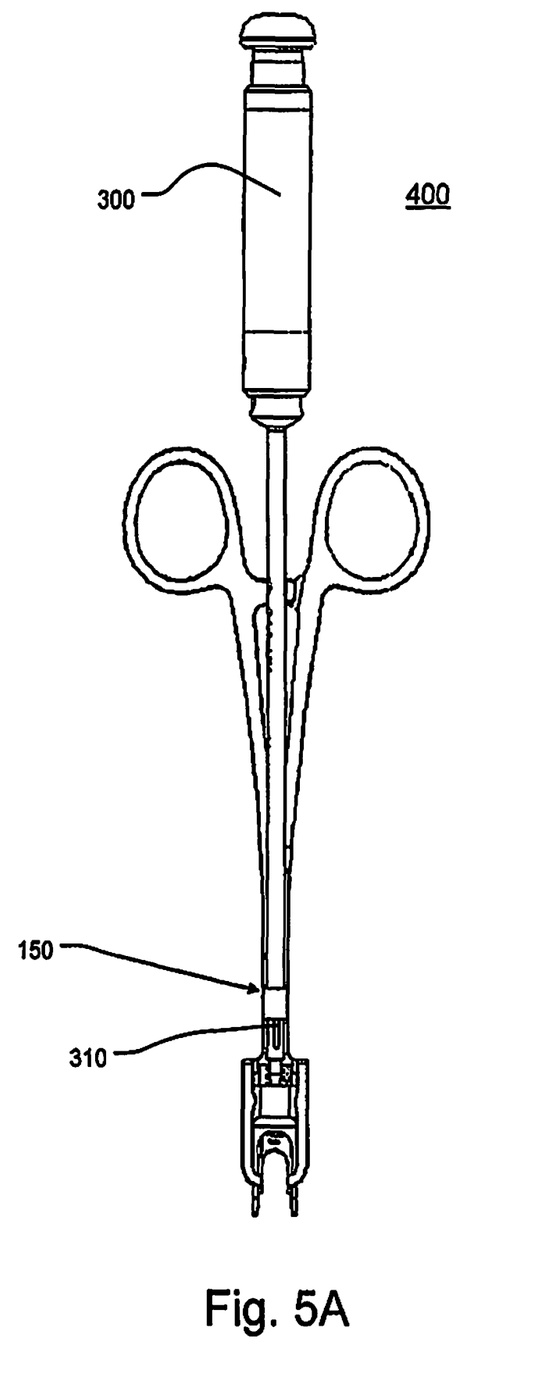
FIG. 5A shows a front view of an example of a distractor system, constructed according to the principles of the disclosure.
Figure 5B:
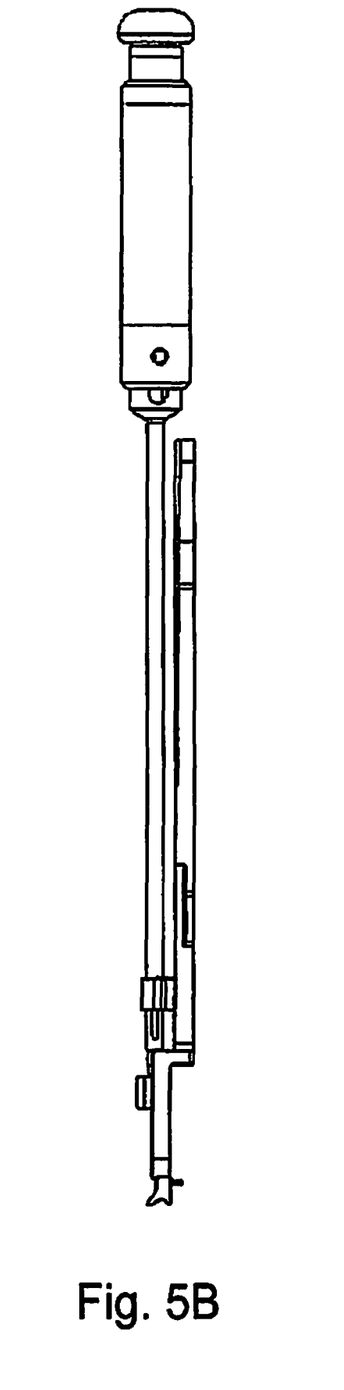
FIG. 5B shows a side view of the distractor system of FIG. 5A.

FIG. 5A shows a front view of a distractor system 400, constructed according to the principles of the disclosure. The distractor system 400 may include the distractor holder 100, the distractor device 200, and the driver 300. FIG. 5B is a side of the distractor system 400.

According to an aspect of the disclosure, the distractor system 400 may be implemented as follows. The distractor device 200 may be assembled, as discussed above, and nested in the distractor holder tip 160 (shown in FIG. 4A). In this regard, the protrusions 162-166 on the distractor holder 100 may be aligned and engaged with the recesses 214, 222, 250 on the distractor device 200 to provide, e.g., six points of fixation. The scissor members 110, 120 may be closed and locked (e.g., via locking member 130) to securely hold the distractor device 200 in place in the distractor holder tip 160. The actuating bar 280 may be adjusted to its zero position (e.g., shown in FIG. 3B).

The distractor holder 100, together with the distractor device 200, may be used to control and maintain a distraction of an intralaminar space during, e.g., an open door laminoplasty procedure. For example, after a surgeon cuts through the lamina of a cervical or upper thoracic spine and then makes a partial cut on the contralateral side, the distractor device 200 may be placed in the cut and used to distract and hold that space open for extended period of time. In this instance, the distractor device 200 may be positioned proximate to the surgery location—i.e., where a laminar trough cut has been made. The actuating bar 280 may be adjusted using, for example, the driver 300 (shown in FIG. 5A), to extend the actuating bar 280 from the housing 205 of the distractor device 200 to aid insertion of the feet 285 into the laminar trough cut. The kickstands 215, 225 may be placed against and seated on an outer surface of a portion of the cut lamina (on one side of the cut), while the feet 285 may inserted through the cut and positioned proximate to an inner surface of another portion of the cut lamina (on the other side of the cut). Then, after the feet 285 are properly aligned, using the driver 300, the actuator 245 may be rotated to drive and retract the actuating bar 280 into the housing, thereby engaging and pulling a portion of the lamina with the feet 285, distracting a space to a desired dimension. The distractor holder 100 may be temporarily separated from the distractor device 200 by, for example, releasing the locking member 130 and opening the scissor members 110, 120.

The distractor device 200 will maintain the created opening until the driver 300 is used again by inserting the driver portion 310 through the cannula 150 and engaging the actuator 245 to extend the actuating bar 280 and the feet 285, thereby releasing the force on the lamina portion and collapsing the distracted space. The driver portion 310 may include, e.g., a hex-head, a Phillips head, a common head, or the like, that is configured to engage the opening 247 in the actuator 245.

The distractor system 400 provides a unique and novel instrumentation that achieves a task of distracting the intralaminar space during, e.g., a laminoplasty surgery such as an open door laminoplasty surgery. The distractor device 200 may be designed to have a low profile so that multiple instruments can be used side-by-side to successively distract intralaminar spaces at adjacent levels.

While the present disclosure has been described in terms of exemplary aspects, those skilled in the art will recognize that the present disclosure can be practiced with modifications in the spirit and scope of the appended claims. These examples given above are merely illustrative and are not meant to be an exhaustive list of all possible designs, aspects, applications or modifications of the present disclosure.

What is claimed is:

1. A distractor device, comprising:
a housing configured to be disposed within an intralaminar space defined as an area between a first portion of a cut lamina and a second portion of the cut lamina, said housing further including a first kickstand and a second kickstand positioned a distal end of the distractor device and extending from the housing in a first direction, the second kickstand separated a distance from the first kickstand in a direction perpendicular to a longitudinal axis of the housing, wherein the first kickstand is configured to engage the first portion of the cut lamina;
an actuating bar having a longitudinal member and a pair of feet disposed distally to the longitudinal member, wherein the pair of feet are positioned at a distal most end of the actuating bar near the first kickstand of the housing at the distal end of the distractor device in one configuration, wherein the pair of feet extend from a surface of the actuating bar in a second direction opposite the first direction beyond any other portion of the actuating bar and are configured to engage the second portion of the cut lamina; and
an actuator independent from the actuating bar that engages and drives the actuating bar, wherein actuation of the actuator causes only axial displacement of the actuating bar along the longitudinal axis of the housing, wherein rotation of the actuator causes the pair of feet of the actuating bar to retract away from the first kickstand and move closer to the actuator, and wherein the pair of feet are configured to pull the second portion of the cut lamina while the first kickstand maintains a position of the first portion of the lamina during rotation of the actuator,
wherein in a configuration where the pair of feet are positioned near the first and second kickstands at the distal end of the distractor device, the first and second kickstands and pair of feet are both located at a distal tip of the distractor device and are oriented in opposing directions relative to the longitudinal axis of the housing.

2. The distractor device of claim 1, wherein at least one of the actuator and the actuating bar comprise a threading.

3. The distractor device of claim 1, wherein the actuator comprises a threaded bolt.

4. The distractor device of claim 3, wherein the threaded bolt has a substantially flat surface on one side and a substantially flat surface and an engageable opening on an opposite side.

5. The distractor device of claim 1, wherein the housing comprises a recess, and when connected to a distractor holder, the recess engages a protrusion on the distractor holder.

6. The distractor device of claim 1, wherein the housing comprises a plurality of recesses, and when connected to a distractor holder, the plurality of recesses are engaged with a plurality of respective protrusions on the distractor holder to provide multiple points of fixation.

7. The distractor device of claim 6, wherein the multiple points of fixation comprise at least four points of fixation.

8. The distractor device of claim 6, wherein the distractor holder comprises a cannula for receiving a driver to engage the actuator.

9. The distractor device of claim 1, wherein the actuating bar comprises a plurality of threads and, when actuating the actuator to cause axial displacement of the actuating bar along the longitudinal axis of the housing, the plurality of threads are engaged and driven by threads on the actuator.

10. The distractor device of claim 1, wherein the actuating bar includes a longitudinal member having a flat portion and a plurality of threads.

11. The distractor device of claim 1, wherein the actuating bar is positioned inside the housing.

12. The distractor device of claim 1, wherein the longitudinal axis is a central longitudinal axis, and the actuator is positioned centrally along the central longitudinal axis of the housing.

13. The distractor device of claim 1, wherein the pair of feet includes a first foot and a second foot separated a distance from the first foot in a direction perpendicular to the longitudinal axis of the housing.

14. A distractor device, comprising:
a housing that includes a first kickstand and a second kickstand positioned at a distal end of the distractor device and extending from the housing in a first direction, the second kickstand separated a distance from the first kickstand in a direction perpendicular to a longitudinal axis of the housing, wherein the first kickstand and the second kickstand are configured to engage a first portion of an intralaminar space;
an actuating bar having a longitudinal member, a first foot, and a second foot separated a distance from the first foot in a direction perpendicular to the longitudinal axis of the housing, wherein the first foot and the second foot are disposed distally to the longitudinal member, wherein the first foot is positioned at a distal most end of the actuating bar near the first kickstand of the housing and the second foot is positioned at the distal most end of the actuating bar near the second kickstand of the housing at the distal end of the distractor device in one configuration, wherein the first foot and the second foot extend from a surface of the actuating bar in a second direction opposite the first direction beyond any other portion of the actuating bar and are configured to engage a second portion of the intralaminar space opposing the first portion of the intralaminar space; and
an actuator independent from the actuating bar that engages and drives the actuating bar, wherein actuation of the actuator causes only axial displacement of the actuating bar along the longitudinal axis of the housing, wherein rotation of the actuator causes the first foot of the actuating bar to retract away from the first kickstand and the second foot of the actuating bar to retract away from the second kickstand and move closer to the actuator,
wherein the first kickstand and the first foot are oriented in opposing directions relative to the longitudinal axis of the housing and the second kickstand and the second foot are oriented in opposing directions relative to the longitudinal axis of the housing,
wherein the first foot and the second foot are configured to pull the second portion of the intralaminar space upon rotation of the actuator while the first kickstand and the second kickstand maintain a position of the first portion of the intralaminar space.

15. The distractor device of claim 14, wherein the longitudinal axis is a central longitudinal axis, and the actuator is positioned centrally along the central longitudinal axis of the housing.

16. A distractor system, comprising:
- a distractor holder having a cannula and a holder tip, wherein the cannula is configured to receive and allow a portion of a driver to pass therethrough, and wherein the holder tip includes a pair of holding protrusions;
- a housing configured to be disposed within an intralaminar space defined as an area between a first portion of a cut lamina and a second portion of the cut lamina, said housing further including a first kickstand and a second kickstand positioned a distal end of the distractor device and extending from the housing in a first direction, the second kickstand separated a distance from the first kickstand in a direction perpendicular to a longitudinal axis of the housing, wherein the first kickstand is configured to engage the first portion of the cut lamina, wherein the housing further comprises a pair of recesses configured to receive the pair of holding protrusions;
- an actuating bar having a longitudinal member and a pair of feet disposed distally to the longitudinal member, wherein the pair of feet are positioned at a distal most end of the actuating bar near the first kickstand of the housing at the distal end of the distractor device in one configuration, wherein the pair of feet extend from a surface of the actuating bar in a second direction opposite the first direction beyond any other portion of the actuating bar and are configured to engage the second portion of the cut lamina; and
- an actuator independent from the actuating bar that engages and drives the actuating bar, wherein actuation of the actuator causes only axial displacement of the actuating bar along the longitudinal axis of the housing, wherein rotation of the actuator causes the pair of feet of the actuating bar to retract away from the first kickstand and move closer to the actuator, and wherein the pair of feet are configured to pull the second portion of the cut lamina while the first kickstand maintains a position of the first portion of the lamina during rotation of the actuator,
- wherein in a configuration where the pair of feet are positioned near the first and second kickstands at the distal end of the distractor device, the first and second kickstands and pair of feet are both located at a distal tip of the distractor device and are oriented in opposing directions relative to the longitudinal axis of the housing.

* * * * *